United States Patent [19]

Hoshino et al.

[11] Patent Number: 5,130,234
[45] Date of Patent: Jul. 14, 1992

[54] METHOD OF QUANTITATIVE DETERMINATION UTILIZING ENZYME AGGREGATION

[75] Inventors: Nobuhiro Hoshino; Yoko Inaba, both of Funabashi; Shunichi Takewaki, Chiba; Yukito Ochiai, Narashino, all of Japan

[73] Assignee: Iatron Laboratories, Inc.

[21] Appl. No.: 399,440

[22] Filed: Aug. 28, 1989

Related U.S. Application Data

[63] Continuation of Ser. No. 724,020, Apr. 17, 1985, abandoned, which is a continuation of Ser. No. 452,435, Dec. 23, 1982, abandoned.

[30] Foreign Application Priority Data

Jan. 14, 1982 [JP] Japan ................................ 57-3314

[51] Int. Cl.$^5$ ................. G01N 33/536; G01N 33/542
[52] U.S. Cl. ....................................... 435/7.9; 435/28; 435/972; 436/501; 436/536; 436/537; 436/819
[58] Field of Search ................. 435/4, 7, 28, 184, 188, 435/7.9, 962, 963, 7.71, 972; 436/501, 512, 518, 536, 537, 538, 539, 540, 819

[56] References Cited

U.S. PATENT DOCUMENTS

| | | | |
|---|---|---|---|
| 4,134,792 | 1/1979 | Boguslaski et al. | 436/537 |
| 4,193,982 | 3/1980 | Avrameas et al. | 424/12 |
| 4,208,479 | 6/1980 | Zuk et al. | 435/7 |
| 4,275,149 | 6/1981 | Litman et al. | 435/7 |
| 4,299,916 | 11/1981 | Litman et al. | 435/6 |
| 4,302,534 | 11/1981 | Halmann et al. | 435/6 |
| 4,359,457 | 11/1982 | Neville, Jr. et al. | 424/85 |
| 4,401,764 | 8/1983 | Smith | 436/500 |
| 4,423,143 | 12/1983 | Rubenstein et al. | 435/7 |
| 4,444,878 | 4/1984 | Paulus | 435/7 |

OTHER PUBLICATIONS

Annals of Clinical Biochemistry 16, 221–239 (1979) M. J. O'Sullivan et al. "Enzyme immunoassay: a review".

*Primary Examiner*—David Saunders
*Attorney, Agent, or Firm*—Michael N. Meller

[57] ABSTRACT

A quantitative determination of a substance is performed in a homogeneous system based on a change in enzyme activity; differences between the activity of a free enzyme and that of an enzyme bound by an aggregation or chemical bonding are observed. A peroxidase-labeled antibody and antigen system is one of of the typical example. Since the reaction is effected in a homogeneous system, the amount of antigen can be easily measured by the difference of enzyme activity.

6 Claims, 2 Drawing Sheets

METHOD OF QUANTITATIVE DETERMINATION UTILIZING ENZYME AGGREGATION

CROSS REFERENCE TO RELATED APPLICATIONS

This application is a continuation of application Ser. No. 724,020, filed Apr. 17, 1985 and now abandoned, which is a continuation of application Ser. No. 452,435, filed Dec. 23, 1982 and now abandoned.

BACKGROUND OF THE INVENTION

This invention relates to a homogeneous analytical method for quantitative determination of substances contained in humors. More particularly the invention relates to an analytical method for the determination of antigens or antibodies in a homogeneous system which method comprises carrying out an antigen-antibody reaction using an enzyme-labeled antigen or antibody and measuring by a principally optical procedure changes in enzyme activity which takes place as a result of aggregation of the material.

The term "aggregation" used in this invention refers to association or amassing of a substance around an enzyme to such an extent as to exert a local change in enzyme activity and, for instance, it refers to immunological agglutination reactions involving biological factors such as agglutinin and other types of agglutination reactions such as those resulting from chemical cross-linking reactions.

Various methods have been proposed for immunologically determining substances contained in humors making use of an antigen-antibody reaction. For instance, methods based on the quantification of precipitate or agglutinate, such as capillary precipitation method, immunonephelometry, nephelometric immunoassay, latex agglutination method, single radial immunodiffusion, and the like are known as long-established techniques, and more recently there have been developed and widely used highly advanced methods, such as radio-immunoassay or enzyme immunoassay, which make accurate determination of even trace components possible by use of a labeled antigen or antibody. However, any of these methods has its own merits and demerits; some involve the problem in sensitivity and others are complicated in operation or have the problem in disposal of radioactive substances, and thus these known methods were unsuited or inconvenient for use in ordinary clinical tests.

SUMMARY OF THE INVENTION

As a result of more extensive studies conducted with the above-described background facts in view, the present inventors found that a difference in enzyme activity is seen between the case where an enzyme with labeled antigen or antibody remains alone and the case where the enzyme has undergone an aggregation as a result of an antigen-antibody reaction, with the enzyme activity being increased with progress of such aggregation, and this finding has led us to the attainment of this invention. Thus, the present invention provides a method for quantitative determination of a target substance according to which an aggregation reaction is performed between the target substance and a receptor having specific conjugation activity to said substance, with an enzyme being conjugated to one of said two materials, and the quantity of the target substance is determined from the consequent change in enzyme activity.

DETAILED DESCRIPTION OF THE INVENTION

Figure 1:
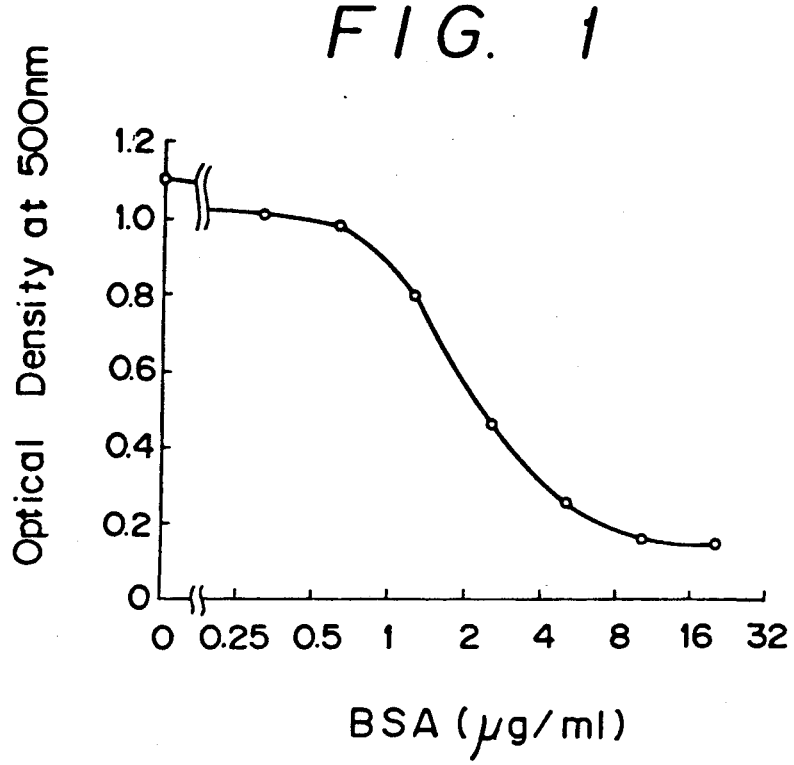
FIG. 1 shows a standard curve for BSA as drawn up based on the results of competitive homogeneous determination of BSA.

As described above, the present invention is based on the finding that the enzyme activity increase quantitatively in accordance with the degree of immunological aggregation, and realizes a homogeneous immunological method by selection of substrate concentration so as to inhibit and keep suppressed the enzyme activity in a state where no aggregation takes place.

Since the change in enzyme activity according to this invention is very sharp and occurs proportionally to a very slight change in the amount of the aggregate, it is possible to determine even trace components of fluid sample from organisms. When viewed from the fact that an antigen-antibody reaction is assayed in a homogeneous system by using an enzyme, the method of this invention appears analogous to the conventional homogeneous enzyme immunoassay, but the method of this invention is totally different in reaction mechanism from the conventional method. That is, the conventional method makes use of steric hindrance which inhibits the substrate from being conjugated to the active site of the enzyme, whereas the method of this invention is based on the change in enzyme activity that takes place according to said immunological aggregation, and this novel method has made it possible to determine a macromolecular antigen by using a low-molecular substrate for the enzyme. The change in enzyme activity begins upon complexing of one molecule of the antigen, which is the target material, to the enzyme-labeled antibody and increases in accordance with the progress of the agglutination reaction or aggregation, so that addition of a reaction promoter such as polyethylene glycol is effective for shortening the time required for the determination.

Various kinds of enzyme can be used in this assay procedure, and it is not difficult for the researchers to select pertinent one from such enzymes. Peroxidase, for example, is one of the preferred enzymes for use in this assay.

Known methods may be used for the monitor of enzyme activity in this invention, but in case of using peroxidase as enzyme, it is recommended to adopt a method where the optical density of the produced color is measured by using as substrate a peroxide such as hydrogen peroxide or urea peroxide in a concentration in excess of the optimal concentration and can inhibit free enzyme while using a phenol such as phenol or p-chlorophenol as hydrogen donor and 4-aminoantipyrine or the like as a coupler that matches with the phenol used. This method is the most effective one that can be applied to this invention.

Known cross linking reagents may be used for the preparation of an enzyme-labeled antigen or antibody. Preferred examples are glutaraldehyde, carbodiimide, bismaleimides and other reagents having two different functional groups. It is also an effective method to form an aldehyde group by oxidizing the carbohydrate group of peroxidase with periodic acid. The enzyme is labeled in a state where the reactivity of the antigen or antibody is maintained by using said reagent.

No limitations are imposed to the molecular weight of the target material to be determined in this invention, and the method of determination is diversified according to the type of the target material used. Shown hereinbelow are some typical examples thereof which are, however, not intended to limit the invention in any way.

I. Utilization of competitive reactions (1) Determination of a low-molecular antigen by using an enzyme-labeled antigen An enzyme-labeled antigen with at least two antigen molecules bonded to one molecule of enzyme is prepared for the determination of an antigen having one recognizable antigenic determinant on the antigen molecule, such as steroid hormons or various kinds of drugs.

When the enzyme-labeled antigen is added to the target material, namely a target antigen and its antibody to induce a competitive agglutination reaction, the enzyme activity can be measured by the addition of the substrate as a function of the quantity of the target antigen, so that it is possible to calibrate the amount of the antigen by using the standard curve. In this case, the enzyme-labeled antigen acts as a polyvalent antigen.

(2) Determination of a macromolecular antigen by using an enzyme-labeled antigen:

In the case of macromolecular antigens such as proteins, there exist a number of recognizable antigenic determinants on the same antigen, so that the number of antigen molecules bonded to one molecule of enzyme may be one or more. It is possible in this case to monitor the target antigen by inducing a competitive reaction by the same operation as in the preceding case 1–(1).

2. Utilization of non-competitive reactions (1) Determination of a macromolecular antigen by using an enzyme-labeled antibody For the determination of a target antigen having at least two recognizable antigenic determinants, an antibody corresponding to such an antigen is labeled with an enzyme. When an agglutination reaction is induced between the target antigen and the enzyme-labeled antibody, three-dimensional conjugation occurs between said antigen and antibody to enhance the degree of agglutination, causing a large change in enzyme activity. It is thus possible to determine the target antigen from such variation in enzyme activity. This is not a competitive reaction type determination although it is a sort of homogeneous immunological method.

(2) Determination of a macromolecular antigen by using a hybrid antibody and an enzyme For determining a macromolecular antigen such as protein, a hybrid antibody is prepared from an antibody corresponding to the target antigen and an antibody corresponding to the enzyme used, and the three components, namely target antigen, enzyme and hybrid antibody, are subjected to a non-competitive reaction and the target antigen is determined from the resulting change in enzyme activity. In this case, the enzyme can be used without being conjugated.

(3) Determination of antibodies

By using the enzyme-labeled antigen of 1-(1) in the case of an antibody corresponding to a low-molecular antigen and the enzyme-labeled antigen of 1-(2) in the case of an antibody corresponding to a macromolecular antigen, an agglutination reaction is induced between such antibody of unknown quantity and said enzyme-labeled antigen and the quantity of the antibody is determined from the consequent change in enzyme activity.

In the antigen-antibody agglutination reaction, a change in quantity of one of the two reactants (antigen or antibody) necessarily results in a corresponding change in quantity of the other reactant to provide the optimal ratio of the two reactants. By making use of this phenomenon, it is possible to shift the measurable range of the target antigen by adding an unlabeled antibody to the enzyme-labeled antibody. More definitely, in the presence of free antibody, the enzyme-labeled antibody is reacted with target antigen. The enzyme activity can be measured by the addition of the substrate. It is noted that the greater the amount of the unlabeled antibody added, the further shifts the measurable range toward the high concentration side of the target antigen. This makes it possible to determine the target antigen without dilution of the fluid sample.

When an enzyme-labeled antibody of a known quantity is reacted with an antigen non-competitively, an agglutination reaction hardly takes place in the region where the antigen is present in excess, and hence the change in enzyme activity is decreased. This gives rise to the operational incommodity to necessitate dilution of the specimen to a measurable range in case the area in which the substance to be determined exists is extensive, for example, in the case of measuring the concentration of $\alpha$-fetoprotein in blood. In such a case, it becomes possible to make determination over a wide range when an enzyme-labeled antibody of a known quantity and an antigen of an unknown quantity are reacted, followed by a further reaction by adding an unlabeled antibody of a known quantity.

The present invention is described in further detail hereinbelow by way of the embodiments thereof.

EXAMPLE 1

Competitive assay of bovine serum albumin (hereinafter referred to as BSA)

(a) Preparation of BSA labeled with horseradish peroxidase (hereinafter referred to as HRP)

5 mg of HRP was treated according to a method of Nakane et al. (The J. of Histochem. & Cytochem., 22-12, 1084–1091, 1974) to have its carbohydrate groups converted into an aldehyde, and 3 mg thereof and 5 mg of crystallized BSA (a product of Sigma) were reacted in a carbonate buffer of pH 9.5 at 25° C. for 2 hours and then fractionated on a Sephadex G-200 column to obtain an enzyme-labeled antigen.

(b) Determination of BSA 0.05 ml each of the serially diluted specimens of BSA prepared with a phosphate buffered saline (pH 7.0, hereinafter referred to as PBS) containing 5.4% of polyethylene glycol 6000 (hereinafter referred to as PEG) were taken into separate test tubes. To the BSA specimen in each test tube were added 0.02 ml of the enzyme-labeled antigen prepared in 1-(a), and 0.02 ml of a BSA antibody (a product by Daco) to effect 15-minute reaction at 37° C., followed by further addition of 2.5 ml of a substrate solution composed of 0.5 mM 4-aminoantipyrine, 50 mM phenol and 35 mM hydrogen peroxide to perform 5-minute reaction at 37° C., and the absorbance at 500 nm was measured. The results shown in FIG. 1 indicate that when the BSA concentration is higher, the agglutination reaction with enzyme-labeled antigen reduces competitively, which results in the lower enzyme activity. There was obtained a standard curve in relation to antigen concentration.

EXAMPLE 2

Non-competitive assay of α-fetoprotein (hereinafter referred to as AFP)

(a) Preparation of anti-AFP antibody F(ab')$_2$ fraction

AFP extracted from blood according to a method of Nishi (Cancer Res., 30, 2507-2513, 1970) and purified, was mixed with an equal amount of Freund's complete adjuvant and immunized against rabbit to obtain an anti-AFP rabbit serum. This antiserum was purified according to a method of Everay et al. (J. Solid-phase Biochem., 2, 45-78, 1977) to get the specific antibody. This antibody was dialyzed against 0.1M acetate buffer (pH 4.5) and, after addition of 2% by weight of pepsin (Boehringer) and, 48-hour digestion at 37° C., passed through a Sephadex G-200 column to obtain an anti-AFP antibody F(ab')$_2$ fraction.

(b) Preparation of maleimide-introduced HRP 9 mg of HRP and 15 mg of tetramethylenediamine were conjugated according to the method of Example 1-(a) to obtain an amino group-introduced HRP. To 2.3 mg of this amino group-introduced HRP was added 1.8 mg of m-maleimidobenzoyl-N-hydroxysuccinimide ester (a product of Pierce Chemicals) and reacted at 30° C. for 30 minutes according to a method of Kitagawa et al. (Clin. Chem., Vol. 6, No. 3, 178-186, 1978) and fractionated with Sephadex G-25 column to obtain a maleimide group-introduced HRP.

(c) Preparation of enzyme-labeled antibody

The antibody F (ab')$_2$ prepared in 2-(a) was reacted with 2-mercaptoethylamine of final concentration of 12.5 mM for 90 minutes, followed on fractionation on a Sephadex G-25 column. To 6 mg of the obtained antibody Fab' was added 1.5 mg of maleimide-introduced HRP prepared in Example 2-(b), and the mixture was reacted at 37° C. for 30 minutes, allowed to stand overnight at room temperature and fractionated with a Sephadex G-200 column to obtain an enzyme-labeled antibody.

(d) Determination of AFP 0.05 ml each of the serially diluted specimens of AFP prepared with PBS were taken into separate test tubes, and to each specimen were added 0.02 ml of PBS containing 10% of PEG and 0.02 ml of the enzyme-labeled antibody prepared in Example 2-(c) for reacting at 37° C. for 15 minutes and further added 2.5 ml of the same substrate solution as used in Example 1-(a) for 5-minute reaction at 37° C., and then the absorbance at 500 nm was measured.

Figure 2:
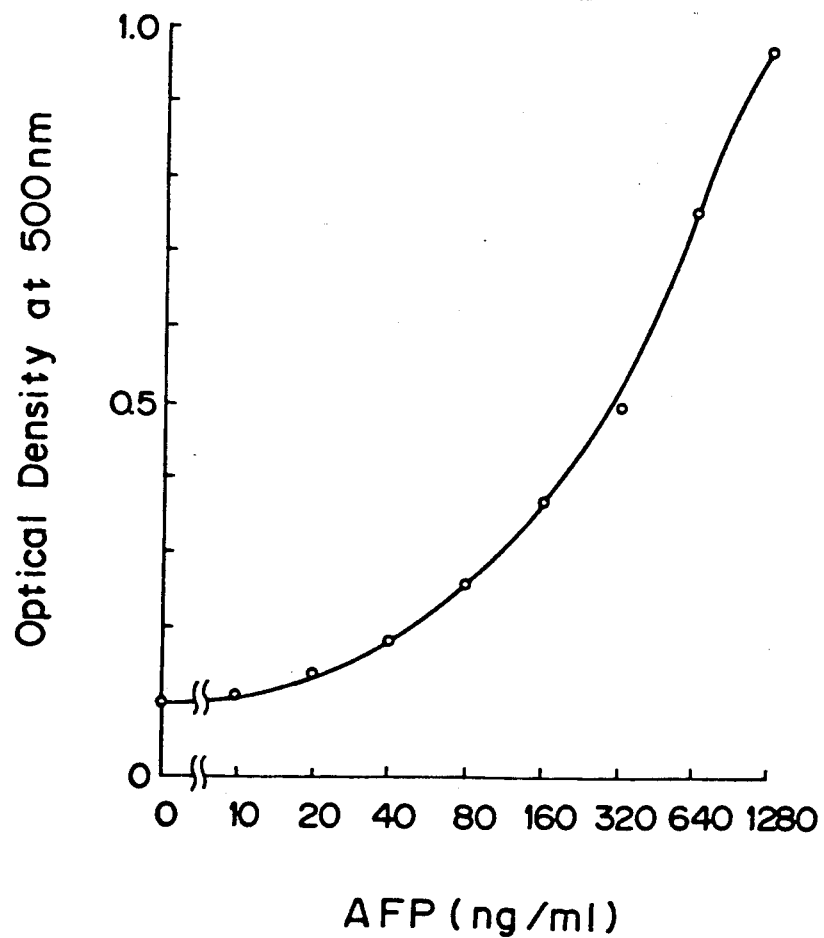
FIG. 2 shows a standard curve for AFP as drawn up based on the results of non-competitive homogeneous determination of AFP.

The results of measurement shown in FIG. 2 gave a standard curve which indicates that the increase of enzyme activity was depended on the AFP concentration. This non-competitive assay has led to establishment of a specific, high-sensitive analytical method.

EXAMPLE 3

Adjustment of a measurable range 0.05 ml of serially diluted specimens of AFP prepared with PBS were taken into separate test tubes. To each specimen were added 0.02 ml of PBS containing 10% of PEG and then 0.04 ml of a solution of enzyme-labeled antibody of Example 2-(b) and a PBS-diluted solution of anti-AFP rabbit serum for 15-minute reaction, and then the enzyme activity was measured by the method of Example 1-(b).

Figure 3:
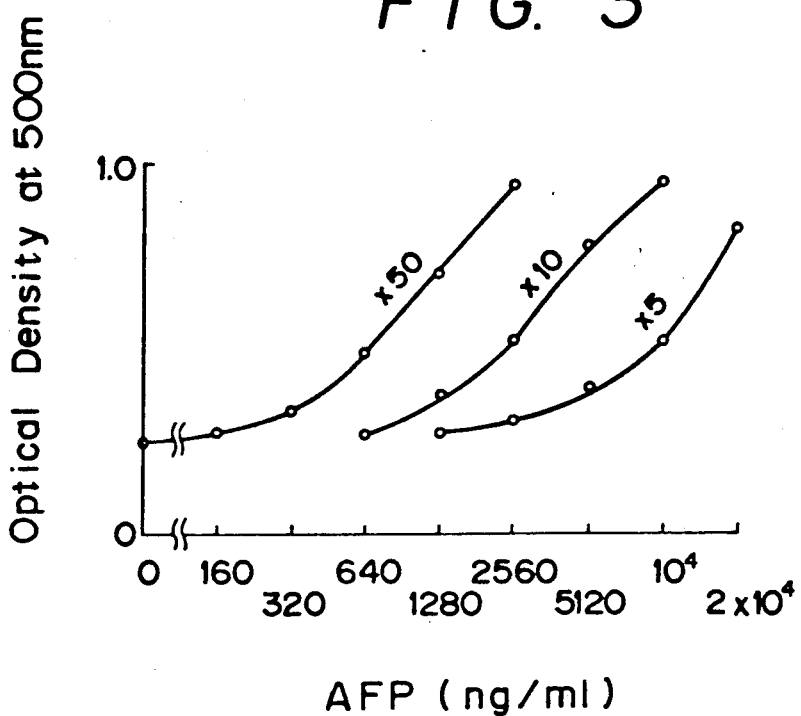
FIG. 3 shows standard curves in case the determination was made by adding an anti-AFP serum to the enzyme-labeled antibody. The figures in the graph indicate the dilution factor of the anti-serum.

The relation between the amount of the antiserum added and the measurable range is shown in FIG. 3. It is seen that addition of an unlabeled antibody to an enzyme-labeled antibody causes a shift of the measurable range. This makes it possible to determine the target antigen without dilution of the specimen.

EXAMPLE 4

Extension of the measurable range

To each of the serially diluted PEG-containing AFP specimens used in Example 3 was added 0.02 ml of the enzyme-labeled antibody of Example 2-(b) for 15 minute reaction at 37° C. To each reaction mixture was added 0.02 ml of anti-AFP serum for additional 15-minute reaction and then the enzyme activity was measured according to the method of example 1-(b).

Figure 4:
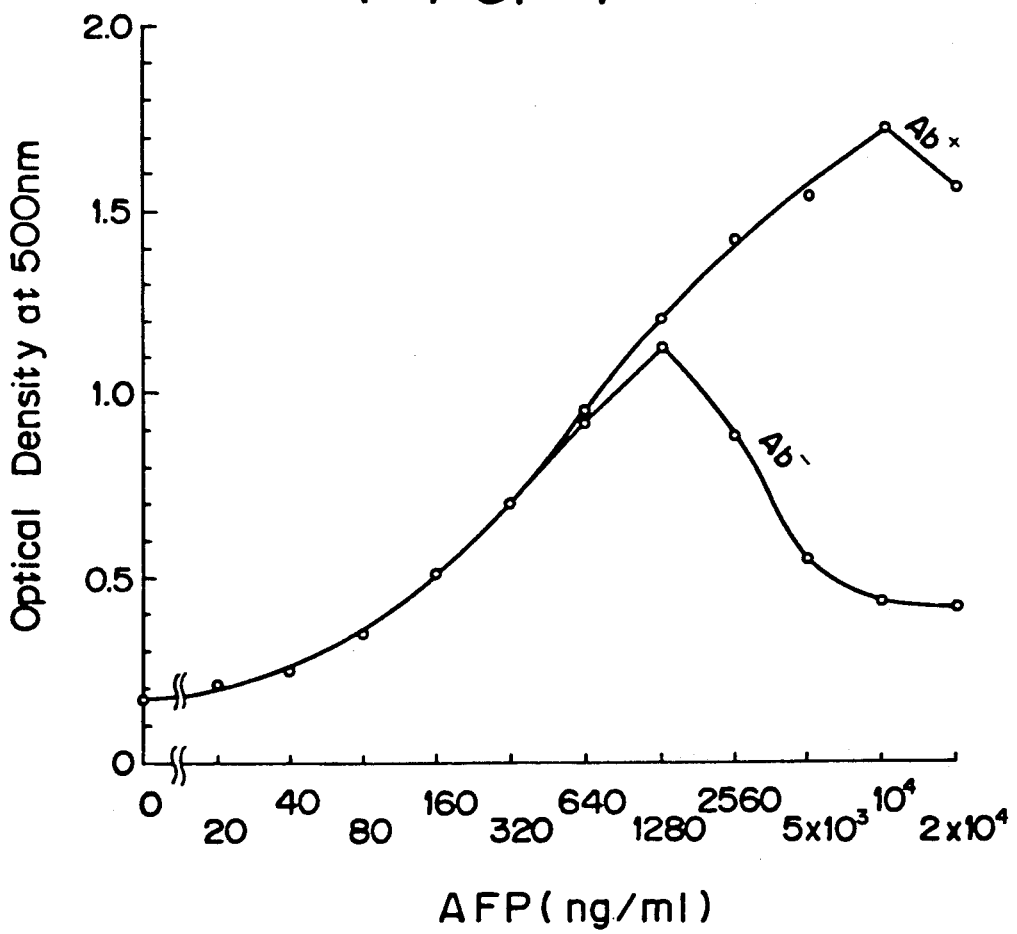
FIG. 4 shows two standard curves, one $Ab^+$ representing the case where the reaction was further continued by adding an anti-AFP serum after the reaction of enzyme-labeled antibody and antigen and the other $Ab^-$ representing the case where no anti-AFP serum was added.

FIG. 4 shows the standard curves obtained when an antibody was added later (Ab+) and not added (Ab−). It is obvious that the measurable range is extended when an antibody is added later.

As described above, the present invention is a novel determination method which can effect an accurate determination on trace components in fluid samples in a homogeneous immunological systems, and this method applies to a wide range of uses. It is to be also noted that the aggregation reaction causing a change in enzyme activity in the method of this invention is not limited to the antigen-antibody agglutination reaction but embraces as well the reactions of material and its receptor combinations such as biotin and avidin or sugar and lectin. Also, for the monitoring of enzyme activity in this invention, there may be employed not only a colorimetric method but also fluorescent technique.

What is claimed is:

1. A method for the quantitative determination of a target material in a sample comprising the steps of:
   (i) reacting in solution phase (a) the target material and (b) a known amount of a peroxidase-labeled receptor having a specific binding activity to the target material to form aggregates of the two components (a) and (b);
   (ii) effecting an enzymatic reaction between the peroxidase contained in the aggregates, a peroxide, a phenol hydrogen donor, and a coupler for said phenol, the peroxide being present in an amount sufficient to inhibit the enzyme in non-aggregated peroxidase labeled receptor to produce an analytically detectable change; and
   (iii) quantitatively determining the target material from the analytically detectable change.

2. A method according to claim 1 wherein the peroxide is in the amount of about 34 mM.

3. A method for the quantitative determination of a target material in a sample comprising the steps of:

(i) reacting in solution phase (a) the target material, (c) a known amount of a receptor having a specific binding activity to the target material, and (d) a known amount of a peroxidase-labeled target material, to form aggregates of the three components (a), (c), and (d);

(ii) effecting an enzymatic reaction between the peroxidase contained in the aggregates, a peroxide, a phenol hydrogen donor, and a coupler for said phenol, the peroxide being present in an amount sufficient to inhibit the enzyme in non-aggregated peroxidase-labelled target material to produce an analytically detectable change; and (iii) quantitatively determining the target material from the analytically detectable change.

4. A method according to claim 3 wherein the peroxide is in the amount of about 34 mM.

5. A method for the quantitative determination of a target material in a sample comprising the steps of:

(i) reacting in solution phase (a) the target material, (e) a known amount of a peroxidase, and (f) a receptor having specific binding activities to both the target material and the peroxidase to form aggregates of the components (a), (e), and (f);

(ii) effecting an enzymatic reaction between the peroxidase contained in the aggregates, a peroxide, a phenol hydrogen donor, and a coupler for said phenol, the peroxide being present in an amount sufficient to inhibit non-aggregated peroxidase to produce an analytically detectable change; and (iii) quantitatively determining the target material from the analytically detectable change.

6. A method according to claim 5 wherein the peroxide is in the amount of about 34 mM.

* * * * *